United States Patent [19]

Kauer

[11] Patent Number: 4,762,881

[45] Date of Patent: Aug. 9, 1988

[54] PHOTOREACTIVE BENZOYLPHENYLALANINES AND RELATED PEPTIDES

[75] Inventor: James C. Kauer, Kennett Square, Pa.

[73] Assignee: E. I. Du Pont de Nemours and Company, Wilmington, Del.

[21] Appl. No.: 1,874

[22] Filed: Jan. 9, 1987

[51] Int. Cl.[4] .................. C08F 283/00; C07C 101/42; C07K 1/04
[52] U.S. Cl. ................. 525/54.11; 562/441; 530/334
[58] Field of Search ............ 525/54.11; 562/441; 530/334

[56] References Cited

PUBLICATIONS

Journal of Medicinal Chem. 16, No. 1 (1973) 60–64.
The Journal of Biol. Chem. 261 (1986) 10695–10700.
Chem. Abstr. vol. 53 (1959) 22509.
Chem. Abstr. vol. 53 (1959) 10559.
J. M. Robert Parker and Robert S. Hodges, *J. Protein Chemistry* 3, 465 (1985).
J. M. Robert Parker and Robert S. Hodges, *J. Protein Chemistry* 3, 479 (1985).

*Primary Examiner*—Delbert R. Phillips

[57] ABSTRACT

Provided is a benzoylphenylalanine of the formula:

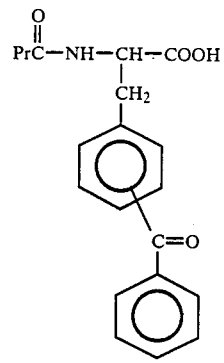

wherein

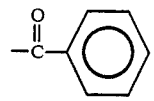

is in the m or p position; and Pr is a protecting group which is easily cleavable in the presence of a peptide bond by a mild acid or base.

This benzoylphenylalanine group is incorporated into a peptide chain which can be attached to a solid substrate having a reactive hydrogen by exposure to low energy ultraviolet light.

17 Claims, No Drawings

PHOTOREACTIVE BENZOYLPHENYLALANINES AND RELATED PEPTIDES

FIELD OF THE INVENTION

This invention relates to benzoylphenylalanines, methods for their preparation and subsequent incorporation into peptides, and processes for using them to attach peptides to substrates.

BACKGROUND OF THE INVENTION

Photoaffinity labeling is a method which has been successful for the identification and localization of macromolecular receptors. For the isolation of peptide receptors and the study of peptide-protein interactions, a chemically-stable amino acid photoaffinity probe which can be incorporated into peptide ligands by both solid phase and solution peptide syntheses is needed. Additional desirable properties include (1) activation by low energy light (300–350 nm), (2) rapid reaction of the activated intermediate, (3) stability in an aqueous environment. The reagents described herein meet these requirements.

The products of this invention are reagents which allow the m or p-benzoylphenylalanine (m or p-Bpa) moiety to be incorporated into a peptide sequence by conventional solid or solution phase peptide synthetic methods. The resulting photoreactive peptide can be used to probe biological recognition sites (e.g. drug receptors or enzyme-active sites) by activation with low energy (300–350 nm) ultraviolet light. The benzoylphenylalanine reagents of this invention will probably find their chief application as laboratory tools. As such, these reagents are useful as photoaffinity labels for studies of the interaction of peptides such as neuropeptide analogs with proteins such as receptors, or they can be used to purify or separate enzymes or receptors from the total population of such materials.

The reagents of this invention are superior to conventional photoaffinity-labeling reagents containing the azide, diazo, or diazirine groups because these conventional reagents suffer from one or more of the following: They are chemically unstable, and inconvenient for solid phase synthesis. They are unstable to normal room lighting conditions or require high-energy light for activation which may result in damage to adjacent biological structures. They react by a one-step process involving the loss of a nitrogen atom and once activated cannot be reactivated. They may rearrange to form a slow-reacting intermediate which may permit the activated peptide to diffuse away from the biological recognition site before establishing a covalent linkage which results in non-specific labeling. On photoactivation, they may form a reactive species which reacts preferentially with water rather than on an adjoining biological structure.

The particular advantages of the benzoylphenylalanine reagents of this invention over previously available photoreactive amino acids are (1) their high chemical stability so that they can be used in conventional solid phase peptide synthesis; (2) their low photoreactivity with water; (3) their activation by low energy light; and (4) their stability in an aqueous environment.

p-Benzoylphenylalanine itself has been previously synthesized by R. E. Galardy [(1973) Ph.D. Thesis, Rockefeller University] but was isolated in very low yield and was prepared via a different synthetic method. The acylated derivative shown below was also disclosed in the thesis. These compounds were not incorporated into peptides because they could not be prepared in large enough quantities.

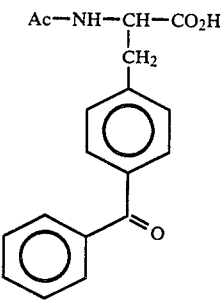

An advantage of the compounds of the present invention is the readily cleavable protecting group which can be removed leaving the rest of the peptide intact.

SUMMARY OF THE INVENTION

According to the present invention there is provided a benzoylphenylalanine of the formula:

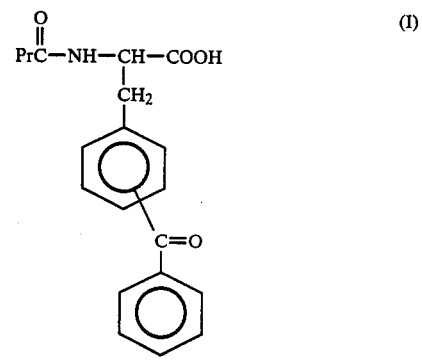

(I)

wherein

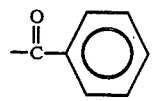

is in the m or p position; and Pr is a protecting group which is easily cleavable in the presence of a peptide bond by a mild acid or base.

Also provided is a photoreactive polypeptide consisting essentially of a polypeptide chain containing at least one benzoylphenylalanine group in the chain having the formula:

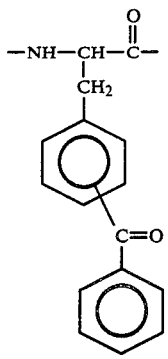
(II)

wherein

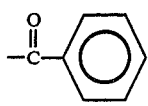

is in the m or p position.

Further provided is a process for preparing a benzoylphenylalanine of Formula (I) which comprises:
(a) contacting benzoylphenylalanine as its L-isomer, D-isomer or DL-isomer with an acid chloride, ester, or anhydride of the protecting group carboxylic acid, PrCOOH, in the presence of sufficient mild base (e.g. amine or bicarbonate salt) to react with the acidic products produced in the reaction; and isolating the protected Bpa derivative (I) by acidification of the reaction mixture followed by filtration or solvent extraction of the product with an organic solvent such as ethyl acetate or chloroform.

Additionally provided is a process for preparing a polypeptide having in the chain a group of Formula (II) which comprises:
(a) contacting a peptide chain of preselected length with a benzoylphenylalanine of Formula (I) in the presence of a coupling agent;
(b) optionally removing the protecting group; and
(c) continuing the peptide chain to a preselected sequence.

Also additionally provided is a process for attaching an aforesaid polypeptide to a solid support which comprises exposing said polypeptide in the presence of a solid substrate having a reactive hydrogen to ultraviolet light of about 300–350 nanometers.

PREFERRED EMBODIMENTS

Preferred benzoylphenylalanines are those of Formula (I) where:
a.

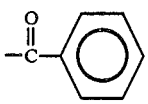

is in the p-position; or
b. Pr is a sterically bulky group preferably OR where R is alkyl of 1-10 carbon atoms, preferably a branched chain alkyl of 4 to 10 carbon atoms such as t-butyl; aralkyl of 7 to 15 carbon atoms such as benzyl or

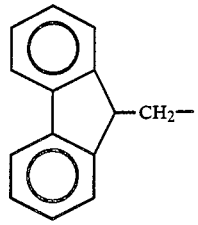

DETAILED DESCRIPTION OF THE INVENTION

According to the present invention, benzoylphenylalanines of Formula (I) can be prepared by the process described below starting with 3-methylbenzophenone, or 4-methylbenzophenone. This method is described for the 4-methyl derivative by J. C. Kauer, et al., *The Journal of Biological Chemistry*, Vol. 261, No. 23, 10695–10700 (1986). The analogous m-Bpa may be similarly prepared from 3-methylbenzophenone.

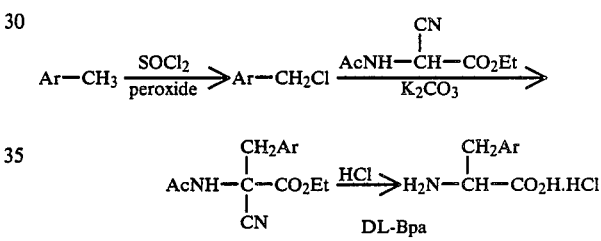

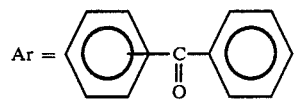

wherein

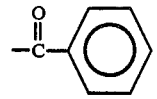

is in the m or p position.

Conversion of DL-Bpa to the acetyl derivative and resolution by hydrolysis with aspergillus acylase I gives L-Bpa which precipitates from solution and N-Acetyl-D-Bpa which remains soluble. After isolation, N-Acetyl-D-Bpa can be hydrolyzed to the corresponding D-Bpa. The DL-isomer, L-isomer or D-isomer can then be protected with a suitable protecting group by contacting a Bpa isomer with an acid chloride, ester, or anhydride of the protecting group carboxylic acid, PrCOOH, in the presence of sufficient mild base (e.g. amine or bicarbonate salt) to react with the acidic products produced in the reaction.

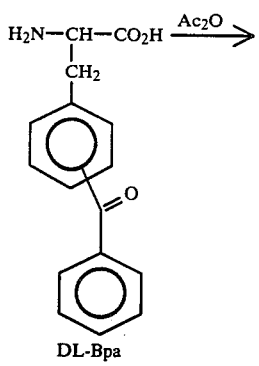

DL-Bpa

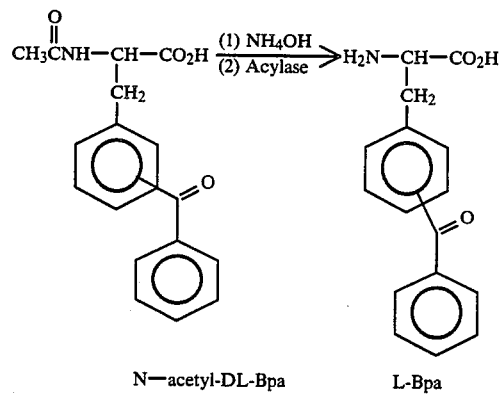

N—acetyl-DL-Bpa    L-Bpa

Protecting groups which can be put on the p and m-benzoylphenylalanine (Bpa) moiety include all protecting groups which are readily cleavable in the presence of a peptide bond, i.e., those groups which are cleaved under mild or standard conditions versus those which require harsh conditions or special reagents, such as an acetyl group. Useful protecting groups (Pr) are bulky groups and preferred groups are branched chain alkyls of 3-10 carbon atoms, preferably 4-10 carbon atoms, of aralkyl groups of 7-15 carbon atoms. Suitable protecting groups are listed in *Synthetic Peptides*, Vol 6, 1982 on page 55. Other bulky protecting groups listed therein which can be used include: furfuryloxycarbonyl (Foc-), 2-bromoethyloxycarbonyl (Bec-), 2-iodoethyloxycarbonyl (Iec-), diisopropylmethyloxycarbonyl (Dmc-), cyclopentylmethyloxycarbonyl, and 2-methylcyclohexyloxycarbonyl.

For establishment of a peptide bond between Bpa and an amino acid residue in a peptide chain of preselected length, the N-protected Bpa derivative of Formula (I), abbreviated as

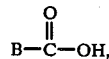

is converted to a reactive intermediate,

as described below, and this reactive intermediate in solution is contacted with the amino residue

either in solution or attached to a solid support (The amino residue may either be the amino residue of a single amino acid, a primary or secondary amine or ammonia, or the amino terminus of a polypeptide chain).

The N-protected Bpa can be converted to a reactive intermediate by treatment with a coupling reagent such as a carbodiimide (e.g., dicyclohexylcarbodiimide), a chloroformate in the presence of a tertiary base, ethoxyacetylene, Woodwards Reagent K, carbonyldiimidazole, thionyldiimidazole or carbonyldi-s-triazole. The reactive intermediate can also be a symmetric or mixed carbonic or phosphorus acid anhydride, or acyl halide or acyl azide, an active ester or o-acylurea.

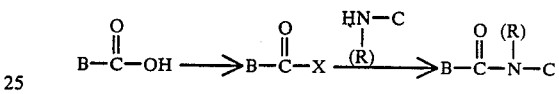

(The R group of the amino residue can be hydrogen, a lower alkyl or benzyl group, part of group C as in proline

and the like).

The symmetric anhydride of the N-protected Bpa can be prepared by allowing two equivalents of the N-protected Bpa derivative to react with one equivalent of diisopropylcarbodiimide in an inert anhydrous solvent such as methylene chloride, tetrahydrofuran or N,N-dimethylformamide. This general reaction is described in E. Gross and J. Meienhofer, *The Peptides*, Vol. 1, Academic Press p. 71 (1979).

The mixed carbonic anydride can be prepared by allowing one equivalent of N-protected Bpa and two equivalents of a tertiary base such as N-methylmorpholine to react with one equivalent of an alkylchloroformate such as isobutyl chloroformate in a dry solvent such as tetrahydrofuran or dioxane at 0° to −20° C. See Gross and Meienhofer, ibid p. 72-75. Mixed anhydrides with phosphorus acid are described in Gross and Meienhofer ibid, p. 75-77.

The acyl azide of N-protected Bpa can be prepared by treatment of the methyl ester with hydrazine followed by treatment with nitrous acid or an alkyl nitrite. The acyl chloride can be prepared by treatment of FMOC-Bpa with thionyl chloride. These general procedures are described by Gross and Meienhofer, ibid, p. 67-70. The methyl ester of the N-protected Bpa may be prepared by treatment of the N-protected Bpa with diazomethane.

Active esters of Bpa can be prepared by treatment of N-protected Bpa in the presence of a carbodiimide (e.g. dicyclohexylcarbodiimide or diisopropylcarbodiimide) with an equivalent of a phenol, a diacylhydroxylamine, an enolic compound or an aza analog of an enol. Suitable reagents include o-nitrophenol, p-nitrophenol, pentafluorophenol, 2,4,5-trichlorophenol, 1-hydroxybenzotriazole, N-hydroxysuccinimide. These and other routes to active esters are described in Gross and Meienhofer, *The Peptides*, Vol. 2, pp. 106, Academic Press (1979).

Bpa o-Acylureas can be prepared by treatment of Bpa with a carbodiimide by the general procedures described in Gross and Meienhofer, *The Peptides*, Vol. 2, pp. 243-246 (1979).

Optionally N-hydroxysuccinimide, 1-hydroxybenzotriazole and other N-hydroxy compounds can be added as catalysts with other coupling reagents such as carbodiimides as is described in Gross and Meienhofer, *The Peptides*, Vol. 1, pp. 251-254, (1979).

Suitable reaction conditions and procedures for solid phase peptide synthesis are described in Gross and Meienhofer, Vol. 2, pp. 1-284, and in J. M. Stewart and J. D. Young. "Solid Phase Peptide Synthesis" 2nd Ed.; Pierce Chemical Co., Rockford, Ill. 1984.

Suitable reaction conditions and procedures for solution phase peptide syntheses are described in M. Bodansky, Y. S. Klausner, M. A. Ondetti, "Peptide Synthesis" 2nd Ed., pp. 13-128 and 177-187, John Wiley and Sons, (1967).

In both of these peptide techniques, the removal of N-protecting groups between the coupling steps is required. For this reason specially designed protecting groups are employed which can be removed without damaging the peptide chain or disturbing side-chain protecting groups. Such preferred N-protecting groups as benzyloxycarbonyl (Cbz) and t-butyloxycarbonyl (t-BOC) can be removed easily by treatment with acidic reagents such as 30% hydrogen bromide in acetic acid and trifluoroacetic acid respectively. Other preferred groups including the fluorenylmethoxycarbonyl group (FMOC) can be removed with mild bases such as secondary amines, e.g., piperidine, diethylamine or morpholine. Such N-protecting groups are described in Gross and Meienhofer Vol. 3, pp. 3-99 (1981).

For instance the t-butoxycarbonyl group can be removed with trifluoroacetic acid in the presence of a scavenger such as phenol, thioanisole, anisole or cresol. The FMOC (fluoroenylmethoxycarbonyl) group can be removed with piperidine alone or in the presence of a solvent such as N,N-dimethylformamide.

In the solid phase synthetic procedure the completed peptide is generally removed from a supporting resin by a reagent which is dependent on the nature of the resin. In the commonly used polystyrene ester resins, for instance, liquid hydrogen fluoride is generally employed both to cleave the peptide from the resin and to free the nascent peptide from side-chain protecting groups. With the polystyrene ether resins (Wang resins), the peptide is cleaved from the resin and freed of side-chain protection by the use of trifluoroacetic acid. With the oxime resin (W. F. DeGrado and E. T. Kaiser, *J. Org. Chem.*, 47, 3258 (1982), ammonia, or an amino ester or peptide ester are commonly used in the presence of acetic acid catalyst to free the peptide amide or ester from the resin.

The ability to place Bpa anywhere in a peptide sequence provides an excellent method for mapping the binding sites of peptide receptors.

Examples 10 and 11 are illustrative of polypeptides into which the Bpa residue has been incorporated.

Bpa-derivatives and Bpa-containing peptides were found to be stable indefinitely when stored at −10° C.

Peptides containing at least one benzoylphenylalanine group can be bound covalently to a solid substrate having a reactive hydrogen by exposure to low energy ultraviolet light (300-350 nm). The benzophenone chromophore in Bpa will react with low energy light to form free radicals which will couple covalently with a solid substrate such as a polymer or protein containing an active hydrogen. The reaction is carried out in a medium (solution phase, solid phase or melt) which is essentially transparent to the ultraviolet light wavelength which is employed. The reaction time may be adjusted to control the degree of incorporation of Bpa peptide into the substrate.

Useful substrates include polymers such as polystryene, polyamides such as 6-nylon or 6,6-nylon, polyolefins such as polyethylene or polypropylene, acrylics such as poly (methyl methacrylate), etc. or proteins, such as bovine or rabbit serum albumin or Keyhole Limpet hemocyanin.

The invention can be understood further by the following examples. In all examples, unless otherwise indicated, all temperatures are in degrees centigrade. NMR Spectra were recorded using either a 360-mHz Nicolet NT or a General Electric QE300 NMR Spectrometer. Amino acid analyses were obtained using a Waters Associates Picotag System. Peptides were synthesized using a Beckman 990B Synthesizer.

EXAMPLE 1

N-t-Butyloxycarbonyl-p-Benzoyl-L-Phenylalanine (BOC-L-BPA)

Part A: p-Chloromethylbenzophenone.

A solution of 100 g (0.51 mol) of p-methylbenzophenone (Aldrich), 130 ml of carbon tetrachloride, 98 g of sulfuryl chloride, and 55 mg of dibenzoyl peroxide was heated at reflux under nitrogen. At 2-h intervals, three additional 50 to 70-mg portions of dibenzoyl peroxide were added. After 18 h a final 50-mg portion of dibenzoyl peroxide was added. After 1 h, unreacted sulfuryl chloride was removed by co-distillation with carbon tetrachloride (b.p. 69°). To the residue containing carbon tetrachloride, was added 5 g of potassium carbonate and 5 g of Woelm basic alumina. The mixture was refluxed for 15 min with stirring, and then filtered hot to give 57 g of crystals after cooling. Recrystallization from ethanol yielded 44.7 g (38%) of colorless crystals (m.p. 95°-96°); m.p. 98° NMR δ4.60 in CDCl$_3$. The product contained about 2% of 4-methylbenzophenone and 0.7% by-product dichloromethylbenzophenone (NMR δ2.45 and 6.75, respectively).

Part B: N-Acetyl-α-Cyano-p-Benzoyl-DL-Phenylalanine Ethyl Ester.

A stirred mixture of 41.9 g (181 mmol) of p-chloromethylbenzophenone, 30.9 g (182 mmol) of ethyl acetamidocyanoacetate, 300 ml of acetone, 17.3 of anhydrous potassium carbonate, and 1.6 g of potassium iodide was refluxed overnight, cooled, and filtered. The solid was washed with acetone, and the combined filtrates were evaporated under reduced pressure. The residue was crystallized from 70 ml of ethanol by cooling to 5°. The resulting product (P59 g) was dissolved in 900 ml of hot ethanol, treated with activated charcoal, filtered, and diluted with 900 ml of hexane to give 45.6 g (69.4%) of colorless crystals (m.p. 151°-152°). Thin layer chromatography (Merck F-254 plates, 95/5, v/v, CHCl$_3$/CH$_3$OH) showed the product to be homogenous (R$_F$ 0.3), and its NMR was consistent with the structure. Anal.: Calcd. for C$_{21}$H$_{20}$N$_2$O$_4$: C, 69.21; H, 5.53; N, 7.69. Found: C, 69.01; H, 5.55; N, 7.81.

Part C: p-Benzoyl-DL-Phenylalanine (DL-Bpa).

A suspension of 45.4 g of the above cyanoester in 188 ml of 8N hydrochloric acid was heated under nitrogen at 100° for 20 h. The mixture was cooled, the solid was collected and washed with 8N hydrochloric acid, then with ethanol and dried to give 36.1 g (95%) of DL-Bpa/HCl (m.p. 202°-204°). The crude hydrochloride dissolved in 480 ml of boiling water was filtered hot, the filtrate was diluted with 480 ml of hot water and immediately neutralized (to pH 7) with 120 ml of 1N sodium hydroxide solution. The mixture was cooled on ice and the resulting fine solid was collected by filtration, washed with water, and vacuum-dried to give 31.0 g (92%) of anhydrous p-benzoyl-DL-phenylalanine (m.p. 217° decomposes). Anal.: Calcd. for $C_{16}H_{15}NO_3$: C, 71.36; H, 5.61; N, 5.20. Found: C, 71.10; H, 5.50; N, 5.11.

Part D: N-Acetyl-p-Benzoyl-DL-Phenylalanine.

To a stirred solution of 41.2 g (153 mmol) of anhydrous DL-Bpa in 600 ml of 1N sodium hydroxide was added 600 g of ice and 52 ml of acetic anhydride. The mixture was stirred for 5 min and was then acidified to pH 3 by the slow addition of 500 ml of 1N hydrochloric acid. The fine crystalline product was filtered, washed with water and dried. Recrystallization from ethanol/hexane yielded 38.04 g (80%) (m.p. 174°-176.5°); $\lambda_{max}$ 258,332 nm ($\epsilon_{258}$ 18,000$M^{-1}$, $\epsilon_{332}$ 180$M^{-1}$ $cm^{-1}$) in isopropyl alcohol. Anal.: Calcd. for $C_{18}H_{17}NO_4$: C, 69.44; H, 5.50; N, 4.50. Found: C, 69.33; H, 5.47, N, 4.49.

Part E: L-Bpa and N-Acetyl-p-Benzoyl-D-phenylalanine.

A suspension of 6.24 g (20 mmol) of acetyl-DL-Bpa in 1.0 liter of water was stirred and 3.5 ml of 4.7N NH4OH was added to bring the pH to 7.5. The solution was filtered and 200 mg of aspergillus acylase I (Sigma) and 5 drops of toluene were added. The solution was stirred at 37° for 18 h and was cooled to 25° and filtered. The damp solid product was dissolved in 50 ml of 0.5N HCl at 70°, Celite was added, the suspension was filtered, and the cake was washed with hot water (50 ml). The clear filtrate was brough to pH 7 by the addition of 7.3 ml of 1N NaOH. The solid was isolated by filtration (see below for filtrate processing), washed with water and a small amount of ethanol, and dried to give 2.36 g (90%) of L-Bpa sesquihydrate (m.p. 178°-179°, $\alpha_D^{25}$ =3.0±0.8°, concentration 1.01 g/100 ml of 1N HCl). Anal.: Calcd. for $C_{16}H_{15}NO_3 \cdot 1.5\ H_2O$: C, 64.85; H, 6.12; N, 4.73. Found: C, 65.09; H, 6.08; N, 4.73. Reaction with acetic anhydride converted this material to the N-acetyl derivative (m.p. 187°-188°, $\alpha_D^{25}$=+50.9±0.8°, concentration 0.98 g/100 ml of ethanol). Anal.: Calcd. for $C_{18}H_{17}NO_4$: C, 69.44; H, 5.50; n, 4.50. Found: C, 69.26; H, 5.58; N, 4.65.

The aqueous filtrate from the acylase hydrolysis described above was acidified to pH 2.4 with HCl. The crystals were isolated (2.91 g) and recrystallized from 500 ml of boiling ethyl acetate to give 2.716 g of N-acetyl-p-benzoyl-D-phenylalanine (87%) (m.p. 186.5°-187° $\alpha_D^{25}$=-49.0±0.8°, concentration 1.05 g/100 ml of ethanol). (In a preliminary experiment a second crystalline modification (m.p. 196.5°-197° was obtained). Anal.: Calcd. for $C_{18}H_{17}NO_4$: C, 69.44; H, 5.50; N, 4.50. Found: C, 69.54; H, 5.46; N, 4.51.

Part F: N-t-Butyloxycarbonyl-p-Benzoyl-L-Phenylalanine (BOC-L-Bpa).

To a stirred solution of 11.95 g of L-Bpa sesquihydrate (40.2 mmol) and 6.3 g of triethylamine in 125 ml of water was added a solution of 11.3 g of 99% 2-(t-butoxycarbonyloxyimino)-2-phenylacetonitrile (Aldrich BOC-ON) in 210 ml of acetone. After 3 h, acetone was removed under reduced pressure and the aqueous solution was extracted three times with ether. The aqueous layer was separated and acidified with 53 ml of 1N HCl to pH 2. The solution was extracted with ethyl acetate and the organic layer was dried (MgSO4) and stripped to give 14.76 g of yellow oil which was triturated for 5 days with petroleum ether. The resulting amorphous solid (13.4 g) crystallized very slowly from 60 ml of ethyl acetate to which 160 ml of hexane was added. The resulting white crystalline BOC-L-Bpa (7.15 g, 48%) melted at 91°-92°, $\alpha_D^{25}$=+18.5±0.8° (concentration of 1.03 g/100 ml of ethanol), $\lambda_{max}$=260,331 nm ($\epsilon_{260}$ 18,000 $M^{-1} cm^{-1}$, $\epsilon_{332}$ 180) in ethanol. Anal. Calcd. for $C_{21}H_{23}NO_5$: C, 68.28; H, 6.28; N, 3.79. Found: C, 67.97; H, 6.05; N, 3.63.

EXAMPLE 2

1-N-t-Butyloxycarbonyl-D-Phenylalanine (BOC-D-Bpa)

Part A: Benzoyl-D-phenylalanine hydrochloride (D-Bpa Hydrochloride).

A mixture of 18.9 g of N-Acetyl-p-benzoyl-D-phenylalanine in 120 ml of 8N hydrochloric acid was heated in a flask immersed in a glycol/water bath heated at 98°-100°. After 6 h the flask was removed and allowed to stand at room temperature overnight. The resulting colorless crystals were filtered and washed with 30 ml of 8N hydrochloric acid then three times with 20 ml portions of 1,2-dimethoxyethane and dried with a stream of dry nitrogen. The white crystalline solid melted at 196°-197°, $\alpha_D^{25}$=-16.8±0.8°, C=0.99 g/100 ml ethanol. Anal.: Calcd. for $C_{16}H_{16}NO_3Cl$: C, 62.85; H, 5.27; N, 4.58; Cl, 11.60. Found: C, 63.07; H, 5.35; N, 4.30; Cl, 11.60.

Part B: N-(t-butyloxycarbonyl)-D-Phenylalanine (BOC-D-Bpa).

A suspension of 1.58 g of D-Bpa hydrochloride in 15 ml of water was stirred and 1.10 ml of triethylamine was added. The solution was stirred and a solution of 1.36 g of 99% 2-(t-butoxycarbonyloximino)-2-phenylacetonitrile (Aldrich BOC-ON) in 25 ml of acetone was added. The solution was stirred for 2.5 h and acetone was then stripped. The aqueous layer was extracted with ether (extract was discarded) and the aqueous layer was acidified to pH 2 with 7 ml of 1N hydrochloric acid. The mixture was extracted with 3×50 ml portions of ethyl acetate, the organic layer was separated, dried (MgSO4) and evaporated to dryness. The oily residue was triturated with petroleum ether for 8 days and gradually solidified. The precipitate was filtered off, washed with petroleum ether and dried to give 1.587 g of a white solid.

The solid was recrystallized from 5 ml of ethyl acetate and 12 ml of hexane to give 779 mg of BOC-D-Bpa, m.p. 129.5-130.5; $\alpha_D^{25}$=-19.1±0.8, C=0.97 g/100 ml ethanol. Anal.: Calcd. for $C_{21}H_{23}NO_5$: C, 68.28; H, 6.28; N, 3.79; Found: C, 67.99; H, 6.21; N, 3.85.

EXAMPLE 3

N-(t-Butoxycarbonyl)-DL-Phenylalanine (BOC-DL-Bpa)

A solution of 10 millimoles (2.873 g) of DL-Bpa monohydrate in 30 ml of water and 2.10 ml of triethylamine was treated with a solution of 2.71 g of 99% 2-(t-butoxycarbonyloximino)-2-phenylacetonitrile (Aldrich BOC-ON) in 50 ml of acetone. The mixture was stirred for 2.5 h and acetone was removed under reduced pressure. The clear yellow aqueous solution was extracted 3 times with ether (discarded). The aqueous solution was acidified to pH 2 and the product was extracted three times with ethyl acetate. The combined extracts were dried (MgSO$_4$) filtered, and evaporated to give 3.675 g of residue which was crystallized from 30 ml of ethyl acetate (solution filtered hot through Celite ®) by the addition of 65 ml of hexane to give 2.154 g of the white crystalline product, m.p. 123°–125°. Anal.: Calcd. for C$_{21}$H$_{23}$NO$_5$: C, 68.28; H, 6.28; N, 3.79. Found: C, 68.01; H, 6.22; N, 3.83.

EXAMPLE 4

N-FMOC-p-Benzoyl-L-Phenylalanine (FMOC-L-Bpa)

A suspension of 593 mg of finely powdered L-Bpa (sesquihydrate) in 20 ml of warm 0.1N sodium hydroxide was cooled to 25° by the addition of ice and a solution of 9-fluorenylmethyl succinimidyl carbonate (FMOC-ONSu) in 20 ml of acetonitrile was added. The solution was stirred and triethylamine was added periodically over 15 minutes to hold the pH at 8.5–9.0. (This required 330 μL of triethylamine.) The clear solution was stirred at 25° for 15 minutes and was then poured into a solution of 5 ml of concentrated hydrochloric acid in 100 ml of ice/water mixture. The resulting suspension was refrigerated. The resulting white crystalline precipitate was filtered off, washed with water and dried with a stream of nitrogen. The crude product (960 mg) was recrystallized from 15 ml of ethyl acetate and 30 ml of hexane to give 819 mg, m.p. 126°–129°, $\alpha_{405}$ $nm^{25}$=+8.3°±2.0, C=1.00 g/100 ml ethanol. Anal.: Calcd. for C$_{31}$H$_{25}$NO$_5$: C, 75.75; H, 5.13; N, 2.85. Found: C, 75.56; H, 5.98; N, 2.65.

EXAMPLE 5

N-FMOC-p-Benzoyl-D-Phenylalanine (FMOC-D-Bpa)

A suspension of 612 mg of finely powdered D-Bpa hydrochloride in 20 ml of warm 0.2N sodium hydroxide was shaken until most of the solid dissolved. Then ice was added to bring the temperature to 25° and a solution of 9-fluorenylmethyl succinimidyl carbonate (FMOC-ONSu) in 20 ml of acetonitrile was added. The mixture was stirred and triethylamine was added dropwise over 15 minutes to hold the pH at 8.5–9.0. All solids eventually dissolved.

The solution was stirred an additional 15 minutes and was poured into a solution of 5 ml of concentrated hydrochloric acid and 100 ml of an ice/water mixture. The resulting mixture was refrigerated overnight and the precipitated solid was broken up, diluted with water to a volume of 250 ml, separated by filtration, and washed with water and dried with a stream of nitrogen. The white solid (961 mg) was recrystallized from ethyl acetate and hexane to give 781 mg of white crystals in two crops, m.p. 126°–129°, $\alpha_{405}$ $nm^{25}$=−9.3°±2.0°, C=1.06 g/100 ml ethanol. Anal.: Calcd. for C$_{31}$H$_{25}$NO$_5$: C, 75.75; H, 5.13; N, 2.85. Found: C, 74.90; H, 5.22; N, 2.80.

EXAMPLE 6

N-FMOC-p-Benzoyl-DL-Phenylalanine (FMOC-DL-Bpa)

A suspension of 539 mg of finely powdered DL-BPa in 20 ml of warm 0.1N sodium hydroxide was shaken until most of the solid dissolved. Ice was added to cool the mixture to room temperature and a solution of 660 mg of 9-fluorenylmethyl succinimidyl carbonate (FMOC-ONSu) in 20 ml of acetonitrile was added. The mixture was stirred and 330 μL of triethylamine was added over a period of 15 minutes to hold the pH at 8.5–9.0. The mixture was stirred an additional 15 minutes, then poured into a solution of 5 ml of concentrated hydrochloric acid in 100 ml of ice/water mixture. The mixture was refrigerated and stirred magnetically for four days and eventually crystallized. The solid was filtered off and washed with cold water and dried with a stream of nitrogen. The resulting white solid (951 mg) was crystallized from ethyl acetate and hexane to give 384 mg of white crystalline monohydrate, m.p. 115°–117°. Anal.: Calcd. for C$_{31}$H$_{27}$O$_6$N: C, 73.07; H, 5.34; N, 2.75. Found: C, 72.84; H, 5.33; N, 2.79.

EXAMPLE 7

N-Carbobenzoxy-L-Bpa

A solution of 2.9 g of L-BPa monohydrate in 100 ml of 0.1N sodium hydroxide was cooled in an ice bath and the following two solutions were added dropwise simultaneously over a period of 1 h: (1) 1.71 of benzyl chloroformate in 25 ml of tetrahydrofuran, (2) 840 mg of sodium bicarbonate in 25 ml of water.

The reaction mixture was stirred for 1 h and allowed to warm to 25°. Then 20 ml of 10% KHCO$_3$ was added. The cloudy aqueous residue was filtered and extracted with ether. The aqueous layer was separated and acidified gradually to pH 1.5 with hydrochloric acid.

The mixture was extracted with ethyl acetate and this extract was dried with magnesium sulfate, filtered and stripped. The residue was triturated with petroleum ether and the product was isolated as a solid (1.8 g).

EXAMPLE 8

N-t-Butoxycarbonyl-m-Benzoyl-L-Phenylalanine (BOC-L-m-Bpa)

Part A: 3-Chloromethylbenzophenone.

A solution of 39.73 g of 3-methylbenzophenone in 50 ml of carbon tetrachloride and 38.94 g of sulfuryl chloride was heated at reflux and five 50 mg portions of dibenzoyl peroxide were added at intervals of 1.0, 3.5, 2, and 17 h. Excess sulfuryl chloride was distilled out by the addition of several portions of carbon tetrachloride. Finally the residue in carbon tetrachloride solution was treated with 5 g of potassium carbonate and 5 g of basic alumina and the mixture was heated at reflux for 15 minutes and then filtered. The filtrate was distilled and a fraction boiling at 147°–157°/0.5 mm was collected which weighed 22.29 g. The distillate crystallized on standing and was recrystallized from 500 ml of hexane to give 8.83 g which melted at 45°–46°. NMR spectroscopic analysis indicated that this material contained 95% of the desired 3-α-chloromethylbenzophenone, 6% 3-α,α-dichloromethylbenzophenone and no unreacted 3-methylbenzophenone. Anal.: Calcd. for C$_{14}$H$_{11}$OCl: C, 72.89; H, 4.81; Cl, 15.37. Found: C, 72.39; H, 4.52; Cl, 15.62.

Part B: N-Acetyl-α-Cyano-3-Benzoyl-DL-Phenylalanine Ethyl Ether

To a solution of 8.00 g of 3-α-chloromethylbenzophenone and 5.9 g of Ethyl acetamidocyanoacetate (EACA) in 60 ml of acetone was added 3.3 g of potassium carbonate and 300 mg of potassium iodide. The mixture was stirred and heated at reflux overnight. The mixture was cooled and filtered, and solids were washed with acetone. The combined filtrates were evaporated under reduced pressure to give 13.00 g of a yellow viscous oil. This product was satisfactory for use in the next step without further purification.

Part C: m-Benzoyl-DL-Phenylalanine (m-Bpa).

A suspension of 12.5 of the above product in 45 ml of 8N hydrochloric acid was heated at 100° in a steam bath overnight. The solution was cooled and neutralized (to pH 7) with 1N potassium hydroxide. The resulting fine yellow crystals were filtered off, washed with water and dried with nitrogen. The crude product (7.338 g) was a fine solid which acquired a strong static charge during transfer. A 4.75 g portion was dissolved in a hot solution of 25 ml of 1N hydrochloric acid in 50 ml of water. The solution was filtered hot and 25 ml of 1N sodium hydroxide was added to the filtrate to give 4.060 g of fine crystals, m.p. 208°–209°. Anal.: Calcd. for $C_{16}H_{15}NO_3$: C, 71.36; H, 5.61; N, 5.20. Found: C, 71.36; H, 5.46; N, 5.18.

Part D: N-Acetyl-m-Benzoyl-DL-Phenylalanine.

A suspension of 11.4 g of m-Benzoyl-DL-phenylalanine in 120 ml of 1N sodium hydroxide was stirred until all solid dissolved. Then 120 g of ice and 9.0 ml of acetic anhydride was added and the mixture was shaken periodically for 5 minutes. The resulting solution was acidified to pH 2 with 1N hydrochloric acid. The resulting solid was filtered off and recrystallized from ethyl acetate/hexane to give 7.848 g of colorless crystals, m.p. 152°–153°. Anal.: Calcd. for $C_{18}H_{17}NO_4$: C 69.44; H, 5.50; N, 4.50. Found: C, 69.50; H, 5.47; N, 4.70.

Part E: Enzymatic Hydrolysis of N-Acetyl-m-Benzoyl-DL-Phenylalanine: m-Benzoyl-L-Phenylalanine.

A solution of 6.24 g of N-acetyl-m-benzoyl-DL-phenylalanine in 1000 ml of water and 1.6 ml of concentrated ammonium hydroxide was adjusted to pH 7.5 by the dropwise addition of 0.5 ml of 1N hydrochloric acid and 500 mg of aspergillus acylase I (Sigma) was added. The suspension was stirred for 4 days at 25° and was filtered to give 2.415 g of crude m-L-Bpa. The crude solid was dissolved in 20 ml of water and 20 ml of 1N hydrochloric acid on the steam bath. Celite ® (Diatomaceous earth) was added and the mixture was filtered hot and 70 ml of hot water was added to the filtrate followed by 20 ml of 1N sodium hydroxide. The pH of the suspension was adjusted to 7 by the dropwise addition of 0.1N hydrochloric acid. The crystalline solid was filtered off, blown dry with nitrogen and weighed 2.175 g, m.p. 232°–233°.

The product of a similar preparation melted at 224.5°–226°, $[\alpha]_D^{25} -2.9 \pm 0.8$, C=0.97 g/100 ml ethanol. Anal.: Calcd. for $C_{16}H_{15}NO_3$: C, 71.36; H, 5.61; N, 5.20. Found: C, 70.64; H, 5.53; N, 5.23.

Part F: N-Acetyl-m-Benzoyl-D-Phenylalanine.

The N-acetyl-m-benzoyl-D-phenylalanine isomer was isolated from the enzymatic hydrolysis filtrate (above) by acidification to pH 2, and extraction with ethyl acetate. The crude product (3.6 g) was recrystallized from ethyl acetate hexane to give 1.085 g, m.p. 145.5°–147° $[\alpha]_D^{25} -46.8 \pm 0.8°$. Anal.: Calcd. for $C_{18}H_{17}NO_4$: C, 69.44; H, 5.50; N, 4.50. Found: C, 69.25; H, 5.38; N, 4.57.

Part G: m-Benzoyl-D-Phenylalanine.

A suspension of 2.0 g of N-Acetyl-m-benzoyl-D-phenylalanine in 15 ml of 8N hydrochloric acid was heated to 100° in the steam bath for 4 h. The suspension was filtered hot, solid was washed with 8N hydrochloric acid, then water. The filtrate was neutralized with 1N sodium hydroxide and yielded 1.503 g of m-benzoyl-D-phenylalanine after water washing and drying under nitrogen, m.p. 230°–231°, $[\alpha]_D^{25} = +3.3 \pm 0.8$ C=0.90 g/100 ml 1N HCl. Anal.: Calcd. for $C_{16}H_{15}NO_3$: C, 71.36; H, 5.61; N, 5.20. Found: C, 70.43; H, 5.34; N, 5.37.

EXAMPLE 9

N-BOC-m-Benzoyl-L-Phenylalanine

A suspension of 2.175 g of m-benzoyl-L-phenylalanine in 25 ml of water and 1.15 g of triethylamine was treated with 3.35 g of BOC-ON in 40 ml of acetone. After 3 h, acetone was removed and the aqueous residue was extracted three times with ether (discarded). The aqueous solution was acidified to pH 2 with 1N hydrochloric acid and extracted with ethyl acetate. The extract was dried (MgSO$_4$) and stripped. The residue was triturated for 7 days with petroleum ether. The waxy insoluble solid was triturated for 14 days with an additional portion of petroleum ether and finally for 7 days with a third portion. The resulting white solid weighed 1.786 g after vacuum drying, $[\alpha]_D^{25} +22.2 \pm 0.9°$, C=0.86 g/100 ml ethanol. Anal.: Calcd. for $C_{21}H_{23}NO_5$:C, 68.28; H, 6.28; N, 3.79. Found: C, 68.01; H, 6.49; N, 3.68.

EXAMPLE 10

Preparation and Purification of Peptide II

A peptide with the sequence LeuLysBpaLysLysLeuLeuLysLeuLeuLysLysLeuLeuLysLeuGly, (Peptide II) was synthesized by the Merrifield method which is described in G. Barany and R. B. Merrifield. The Peptides: Analysis, Synthesis, Biology (Gross and Meienhofer, eds), Vol. 2, pp. 1–284 (1980) using the protecting groups and synthetic protocol described for peptide I (W. F. DeGrado et al., J. Cell. Biochem., 29, 83–93 (1985). The Bpa residue was incorporated using a 3-fold excess of the corresponding BOC-protected symmetric anhydride formed by reaction of 6 eq of BOC-L-Bpa with 3 eq of diisopropylcarbodiimide in CH$_2$Cl$_2$/N,N-dimethylformamide (1/1) for 15 min at 0°. This was allowed to react with the resin and the coupling reaction was complete within 4 h as determined by the ninhydrin test. The peptide was cleaved from the resin by reaction with HF/p-cresol (10:1) at 0° for 60 min. The crude product was purified in a single step by reversed-phase HPLC using a Hamilton PRP-1 semi-preparative column (purchased from Pierce), and a gradient of 35–41% aqueous acetonitrile containing 0.1% trifluoroacetic acid, at 0.33%/min and flow rate of 4.0 ml/min. Fractions containing pure peptide were pooled and lyophilized giving chromatographically homogeneous peptide in 19% overall yield based on the loading of the first amino acid on the resin.

Amino acid analysis (Leu$_{7.70}$ (8), Lys$_{6.82}$ (7), Gly$_{1.06}$ (1)), Edman sequence analysis, and analytical reversed phase HPLC showed that the desired peptide had been obtained in homogeneous form. Fast atom bombardment/mass spectroscopy gave the appropriate parent ion (M+H)$^+$ =2128 indicating that the Bpa residue had been preserved intact through the synthetic and purification procedures. This was confirmed by UV spectroscopy and NMR spectroscopy. Stock solutions of the peptide were stored frozen at −10° in aqueous solution at a concentration of 2 mg/ml. Under these conditions, it was stable for at least 6 weeks.

EXAMPLE 11

Preparation of L-BPA-Morphiceptin Amide (4-BMA)

Part A: BOC-p-Benzoyl-L-Phenylalanine Amide.

A solution of 3.69 g (10 mmol) of BOC-p-benzoyl-L-phenylalanine (L-Bpa) and 1.01 g of N-methylmorpholine in dry tetrahydrofuran was cooled to −20° and 1.36 g of isobutyl chloroformate was added, followed in 5 min by a solution of 1 ml of concentrated ammonium hydroxide in 1 ml of acetone. The mixture was stirred at 0° for 30 min, then solvent was stripped and the residue was shaken with 150 ml of water and 150 ml of ethyl acetate. The organic layer was washed with 5% aqueous citric acid; then with aqueous sodium bicarbonate and dried (MgSO$_4$). Solvent was stripped and the residue (3.434 g) was twice crystallized from ethyl acetate to give 1.8 g of white crystalline BOC-amide as hemihydrate, m.p. 148°-149°. Anal.: (C$_{21}$H$_{24}$N$_2$O$_4$.½H$_2$O), Calcd.: C, 66.82%; H, 6.69%; N, 7.47%. Found: C, 66.80%; H, 6.71%; N, 7.14%.

Part B: p-Benzoyl-L-Phenylalanine Amide Acetic Acid salt.

A 1.0 g portion of the BOC-amide was dissolved in 10 ml of 98% formic acid. After 2 h at 25°, the solution was lyophilized. The residue was successively lyophilized from water and from acetic acid. This final residue was dissolved in 25 ml of methylene chloride and filtered to remove a small amount of p-benzoyl-L-phenylalanine. The solution was used as described in the next section.

Part C: Boc-L-Tyrosyl(t-Butylether)-L-Prolyl-L-Phenylalanyl-p-Benzoyl-L-phenylalanine Amide.

A suspension of 8.6 g (5 mmol) of oxime resin (described in W. F. DeGrado and E. T. Kaiser, *J. Org. Chem.*, 47, 3258 (1982)), 2.652 g of BOC-L-phenylalanine and 5.0 ml of 2.0M diisopropylcarbodiimide (DIC) in 96 ml of CH$_2$Cl$_2$ was shaken gently for 3 days. The resulting resin was filtered off and washed successively with 5×100 ml of 2:1 CH$_2$Cl$_2$/C$_2$H$_5$OH, 3×100 ml CH$_3$OH and dried. Unreacted sites were blocked by shaking for 15 ml with 6.05 ml of C$_6$H$_5$COCl and 9.05 ml of diisopropylethylamine (DIEA) in 100 ml of CH$_2$Cl$_2$. The solid was filtered off and vacuum dried to give 10.1 g of BOC-L-Phe-oxime resin. A 4.69 g portion (1.37 mmol) of the resin was coupled successively with 2.6 mmoles of the symmetric anhydrides of BOC-L-proline (3 h) and BOC-L-tyrosine (t-butyl ether) (17 h) using a Beckman 990B synthesizer and the program of Nakagawa and Kaiser, described in *J. Org. Chem.*, 48, 678 (1983). The symmetric anhydride was prepared by treating 7.2 mmoles of the corresponding BOC-amino acid (Bachem, Switzerland) in 38 ml of CH$_2$Cl$_2$ and 10 ml of dimethylformamide (DMF) with 3.6 ml of 1M DIC in CH$_2$Cl$_2$ at 0°. Note that there is no neutralization step in this program; after the addition of 3.6 mmole of the preformed BOC symmetric anhydride, 4.6 ml of 10% DIEA in CH$_2$Cl$_2$ was added. The resulting BOC-Tyr(tBu)-Pro-Phe-resin was washed with ethanol and after vacuum drying weighed 5.17 g. (Amino acid analysis found: Tyr, 0.301; Pro, 0.272; Phe. 0.292 mmol/g).

A 3.40 mg portion of this resin was added to the p-benzoyl-L-phenylalanine amide acetic acid salt solution in methylene chloride (above) and 58 μl of acetic acid was added. The slurry was shaken gently for 40 h at 25° and filtered. The solid was washed with 2×15 ml CH$_2$Cl$_2$, then with 4×25 ml CH$_3$OH. Combined filtrates were stripped, the residue (1.423 g) in ethyl acetate was washed with 10% citric acid, 5% sodium bicarbonate, dried (MgSO$_4$) and stripped. This residue (1.287 g) was triturated for 3 days with ether. The resulting solid (894 mg) was chromatographed in 75-120 mg portions on 30 g of Merck Kieselgel H using 3% ethanol in chloroform; 8 ml fractions were collected. Pooled fractions 23-26 yielded 480 mg of BOC-Tyr(tBu)-Pro-Phe-Bpa-NH$_2$. Rechromatography of fractions 27-32 produced an additional 104 mg, Rf 0.60 (Silica Gel H, chloroform/methanol 9:1). A 33 mg portion was crystallized from 1 ml ethyl acetate and 1 ml hexane to give 27 mg of white powder, m.p. 115°-121°. NMR 360 mHz (10% CD$_3$OD in CDCl$_3$) δ 7.3-7.8 (m, 9H, Bpa aromatics), 7.1-7.3 (m, 5H, Phe aromatics), 6.89, 7.03 (dd, 4H Tyr aromatics, J=8 Hz), 4.72 (m, H, Tyr α), 4.48 (m, H, Phe α), 4.35 (m, H, Bpa α), 3.35 (m, 2H, Pro δ), 2.9-3.2 (m, 4H, Tyr β+Phe β), 2.75 (m, 2H, Bpa β), 1.75-2.0 (m, 4H, Pro β+γ), 1.36 and 1.48 (d, 9H, Tyr OtBu), 1.31 (s, 9H, BOC CH$_3$). Anal.: (C$_{48}$H$_{57}$N$_5$O$_8$). Calcd.: N, 8.42%. Found: N, 8.42% (combined chromatography fractions 17-19 produced 75 mg of the deletion dipeptide BOC-Tyr(t-Bu)-Bpa-NH$_2$, NMR similar, but lacked Pro and Phe peaks).

Part D: L-Tryosyl-L-prolyl-L-Phenylalanyl-p-Benzoyl-L-Phenylalanine Amide Hydrochloride (4-BMA).

A solution of 106 mg of BOC-Tyr(tBu)-Pro-Phe-Bpa-NH$_2$ in 3 ml of anisole was treated with 0.7 ml of 4N HCl in dioxane. The clear solution gradually deposited 104 mg of crystalline monohydrate which was separated by decantation, washed with ether, and vacuum dried. Amino acid analysis; found: Proline, 1.038, Tyrosine 0.881, Phenylalanine 0.962. Anal: (C$_{39}$H$_{41}$N$_5$O$_6$HCl1H$_2$O) Calcd.: C, 64.14%; H, 5.94%; N, 9.58%; found C, 63.75%; H, 5.69%; N, 9.58%. UV λ$_{max}$(Ethanol, C=0.100 g/100 ml) λ$_{max}$259 nM ε 25000, 332 mM ε=160 (Water, C=0.100 g/100 ml) 265 nM ε16400, 335 nM (sh).

EXAMPLE 12

A solution of 100 mg of a peptide containing BPA in 10 ml of water is placed on a 8 cm diameter sheet of polystyrene placed in a Petri dish placed on a bed of crushed ice (for cooling) and the solution is irradiated from the top by an 8-watt ultraviolet lamp (350 nm "black light" source) held 10 cm above the liquid surface. The solution is exposed to the ultraviolet light for 1 h. The treated polystyrene sheet is removed from the solution and washed with water, and dried. The polystyrene sheet is now coated with a thin film of the peptide chemically bonded to the surface.

What is claimed is:

1. A benzoylphenylalanine having the formula:

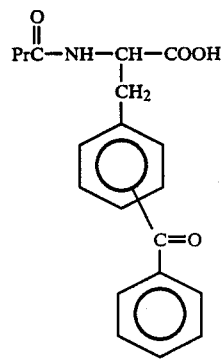

wherein

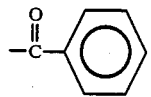

is in the m or p position; and Pr is a protecting group which is easily cleavable in the presence of a peptide bond by a mild acid or base.

2. A benzoylphenylalanine of claim 1 wherein Pr is a bulky protecting group removable by acidic or by basic treatment.

3. A benzoylphenylalanine of claim 2 wherein Pr is OR where R is a branched chain alkyl of 3 to 10 carbon atoms or aralkyl or 7 to 15 carbon atoms.

4. A benzoylphenylalanine of claim 3 wherein

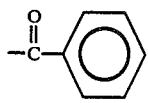

is in the p position and R is a branched chain alkyl group of 4 to 10 carbon atoms.

5. A benzoylphenylalanine of claim 4 wherein R is t-butyl.

6. A benzoylphenylalanine of claim 3 wherein R is benzyl.

7. A benzoylphenylalanine of claim 3 wherein R is fluorenylmethyl.

8. A photoreactive polypeptide consisting essentially of a peptide chain containing at least one benzoylphenylalanine group in the chain having the formula:

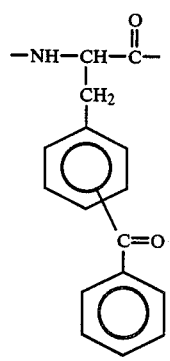

(II)

wherein

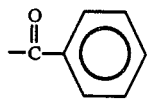

is in the m or p position.

9. A polypeptide of claim 8 wherein

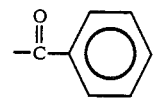

is in the p-position.

10. A process for preparing a photoreactive polypeptide of claim 8 comprising:
(a) contacting a peptide chain of preselected length with a benzoylphenylalanine having the formula:

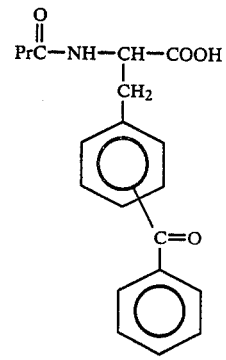

where Pr is defined in claim 1;
(b) optionally removing the protecting group; and
(c) continuing the peptide chain to a preselected polypeptide sequence.

11. A process of claim 10 wherein Pr is OR where R is an alkyl of 1 to 10 carbon atoms or aralkyl of 7 to 15 carbon atoms.

12. A process of claim 11 wherein

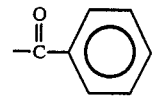

is in the p position and R is a branched chain alkyl group of 4 to 10 carbon atoms.

13. A process of claim 12 wherein R is t-butyl.

14. A process of claim 11 wherein R is benzyl.

15. A process of claim 11 wherein R is fluorenylmethyl.

16. A process for attaching a photoreactive polypeptide to a solid substrate comprising exposing a polypeptide of claim 8 to ultraviolet light of about 300–350 nanometers in the presence of a solid substrate having a reactive hydrogen.

17. A process of claim 16 wherein the solid substrate is a polystyrene, a polyolefin, an acrylic polymer, a polyamide or a protein.

* * * * *